(12) United States Patent
Gros et al.

(10) Patent No.: US 10,755,407 B2
(45) Date of Patent: Aug. 25, 2020

(54) SYSTEMS AND METHODS FOR CAPTURING DEEP LEARNING TRAINING DATA FROM IMAGING SYSTEMS

(71) Applicant: General Electric Company, Schenectady, NY (US)

(72) Inventors: Eric Michael Gros, Waukesha, WI (US); David Erik Chevalier, Menomonee Falls, WI (US)

(73) Assignee: GENERAL ELECTRIC COMPANY, SCHENECTADY, NY (US)

( * ) Notice: Subject to any disclaimer, the term of this patent is extended or adjusted under 35 U.S.C. 154(b) by 285 days.

(21) Appl. No.: 15/884,081

(22) Filed: Jan. 30, 2018

(65) Prior Publication Data

US 2019/0236773 A1  Aug. 1, 2019

(51) Int. Cl.
| | | |
|---|---|---|
| *G06K 9/00* | (2006.01) | |
| *G06T 7/00* | (2017.01) | |
| *G06N 3/08* | (2006.01) | |
| *G16H 30/20* | (2018.01) | |

(52) U.S. Cl.
CPC .......... *G06T 7/0012* (2013.01); *G06N 3/084* (2013.01); *G16H 30/20* (2018.01); *G06T 2207/10081* (2013.01); *G06T 2207/10116* (2013.01); *G06T 2207/20081* (2013.01)

(58) Field of Classification Search
CPC ......... G06T 7/0012; G06T 2207/10081; G06T 2207/10116; G06T 2207/20081; G16H 30/20; G06N 3/084

USPC .......................................................... 382/131
See application file for complete search history.

(56) References Cited

U.S. PATENT DOCUMENTS

| | | | |
|---|---|---|---|
| 2018/0307979 A1* | 10/2018 | Selinger | H04N 7/183 |
| 2019/0042945 A1* | 2/2019 | Majumdar | G06N 3/0635 |
| 2019/0156213 A1* | 5/2019 | Tsuzuku | G06N 3/063 |
| 2019/0236774 A1* | 8/2019 | Gros | G06K 9/6273 |
| 2019/0362522 A1* | 11/2019 | Han | A61B 5/7267 |
| 2019/0370957 A1* | 12/2019 | Manickam | G06T 7/10 |
| 2020/0042362 A1* | 2/2020 | Cui | G06F 17/18 |
| 2020/0118000 A1* | 4/2020 | Schmidt | G06N 3/084 |

OTHER PUBLICATIONS

Jiang, Zheng, et al. "Training sample selection for deep learning of distributed data." 2017 IEEE International Conference on Image Processing (ICIP). IEEE, 2017. (Year: 2017).*
Shorki, R. et al., "Privacy-Preserving Deep Learning," Proceedings of the 22nd ACM Conference on Computer and Communications Security, Oct. 12, 2015, Denver, Colorado, 12 pages.

(Continued)

*Primary Examiner* — Jonathan S Lee
(74) *Attorney, Agent, or Firm* — McCoy Russell LLP

(57) ABSTRACT

Methods and systems are provided for generating deep learning training data with an imaging system. In one embodiment, a method for an imaging system comprises performing a scan of a subject to acquire imaging data, training a deep neural network on the imaging data to obtain updates to the deep neural network, and transmitting the updates to a server for training a central deep neural network. In this way, imaging data may be leveraged for training and developing global deep learning models without transmitting the imaging data itself, thereby preserving patient privacy.

20 Claims, 4 Drawing Sheets

(56) References Cited

OTHER PUBLICATIONS

Konečný, J. et al., "Federated Optimization: Distributed Machine Learning for On-Device Intelligence," Cornell University Library Website, Available Online at https://arxiv.org/abs/1610.02527, Oct. 8, 2016, 38 pages.
Gade, S. et al., "Private Learning on Networks," Cornell University Library Website, Available Online at https://arxiv.org/abs/1612.05236, Dec. 15, 2016, 22 pages.
Gade, S. et al., "Private Learning on Networks: Part II," Cornell University Library Website, Available Online at https://arxiv.org/abs/1703.09185, Mar. 27, 2017, 29 pages.
McMahan, B. et al., "Federated Learning: Collaborative Machine Learning without Centralized Training Data" Google Research Blog Website, Available Online at https://research.googleblog.com/2017/04/federated-learning-collaborative.html, Apr. 6, 2017, 10 pages.
McMahan, B. et al., "Communication-Efficient Learning of Deep Networks from Decentralized Data," Proceedings of the 20th International Conference on Artificial Intelligence and Statistics (AISTATS) 2017, Apr. 20, 2017, Fort Lauderdale, Florida, 11 pages.
Bonawitz, K. et al., "Practical Secure Aggregation for Privacy-Preserving Machine Learning," Proceedings of the 24th ACM Conference on Computer and Communications Security, Oct. 30, 2017, Dallas, Texas, 17 pages.
Konečný, J. et al., "Federated Learning: Strategies for Improving Communication Efficiency," Cornell University Library Website, Available Online at https://arxiv.org/abs/1610.05492, Oct. 30, 2017, 10 pages.

\* cited by examiner

SYSTEMS AND METHODS FOR CAPTURING DEEP LEARNING TRAINING DATA FROM IMAGING SYSTEMS

FIELD

Embodiments of the subject matter disclosed herein relate to non-invasive diagnostic imaging, and more particularly, to the training of deep learning algorithms for imaging systems.

BACKGROUND

Non-invasive imaging technologies allow images of the internal structures of a patient or object to be obtained without performing an invasive procedure on the patient or object. In particular, technologies such as computed tomography (CT) use various physical principles, such as the differential transmission of x-rays through the target volume, to acquire image data and to construct tomographic images (e.g., three-dimensional representations of the interior or the human body or of other imaged structures).

New post-processing techniques can substantially improve the functionality of an imaging system as well as the accuracy of clinical diagnoses. For example, modern deep learning techniques may allow lesions to be accurately detected in tomographic images with a lower image quality, thereby enabling a reduction in radiation dose (and thus a potential reduction in image quality) without sacrificing the diagnostic effectiveness of the imaging system. One notable feature of deep learning algorithms is the ability for the algorithm to improve over time as it is trained on additional imaging data acquired by the imaging system. However, it is difficult to leverage these improvements for other imaging systems, as training the deep learning algorithm typically requires access to the raw imaging data, which potentially includes sensitive patient information.

BRIEF DESCRIPTION

In one embodiment, a method for an imaging system comprises performing a scan of a subject to acquire imaging data, training a deep neural network on the imaging data to obtain updates to the deep neural network, and transmitting the updates to a server for training a central deep neural network. In this way, imaging data may be leveraged for training and developing global deep learning models without transmitting the imaging data itself, thereby preserving patient privacy.

It should be understood that the brief description above is provided to introduce in simplified form a selection of concepts that are further described in the detailed description. It is not meant to identify key or essential features of the claimed subject matter, the scope of which is defined uniquely by the claims that follow the detailed description. Furthermore, the claimed subject matter is not limited to implementations that solve any disadvantages noted above or in any part of this disclosure.

BRIEF DESCRIPTION OF THE DRAWINGS

The present invention will be better understood from reading the following description of non-limiting embodiments, with reference to the attached drawings, wherein below.

DETAILED DESCRIPTION

The following description relates to various embodiments of non-invasive diagnostic imaging. In particular, systems and methods are provided for generating deep learning training data with an imaging system. An example system that may be used to generate and utilize deep learning training data is provided in FIG. 1. A deep neural network, such as the deep neural network depicted in FIG. 2, is trained on imaging data acquired by an imaging system. A method for an imaging system, such as the method depicted in FIG. 3, includes transmitting updates to the deep neural network of the imaging system to a central server for training a central deep neural network. A method for a central server, such as the method depicted in FIG. 4, includes aggregating and averaging such network updates received from a plurality of imaging systems and training a central deep neural network on the average updates. An example of a CT imaging system that may be used to acquire images processed in accordance with the present techniques is provided in FIGS. 5 and 6.

Though a CT system is described by way of example, it should be understood that the present techniques may also be useful when applied to images acquired using other imaging modalities, such as tomosynthesis, MM, C-arm angiography, and so forth. The present discussion of a CT imaging modality is provided merely as an example of one suitable imaging modality.

Figure 1:
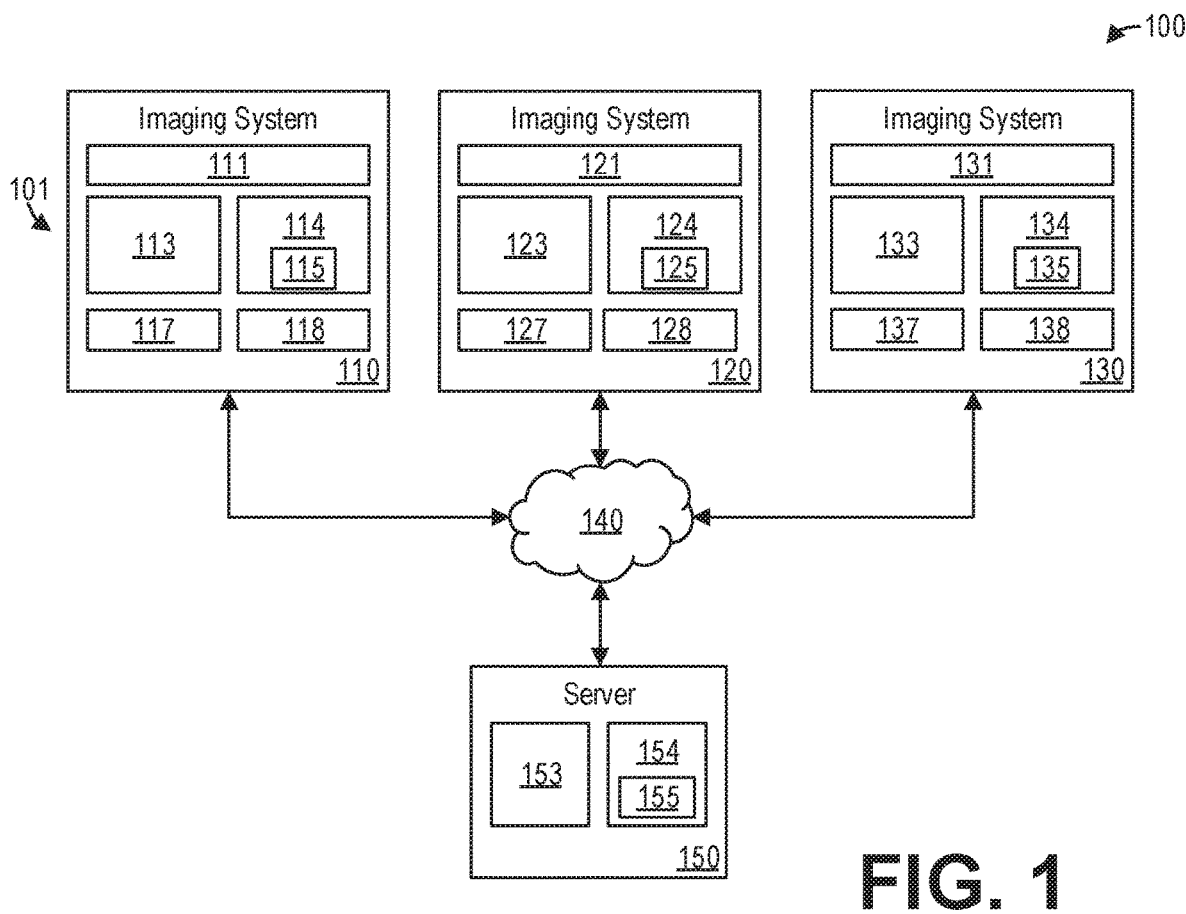
FIG. 1 shows a block schematic diagram of an example system for deep learning training data collection according to an embodiment.
Figure 2:
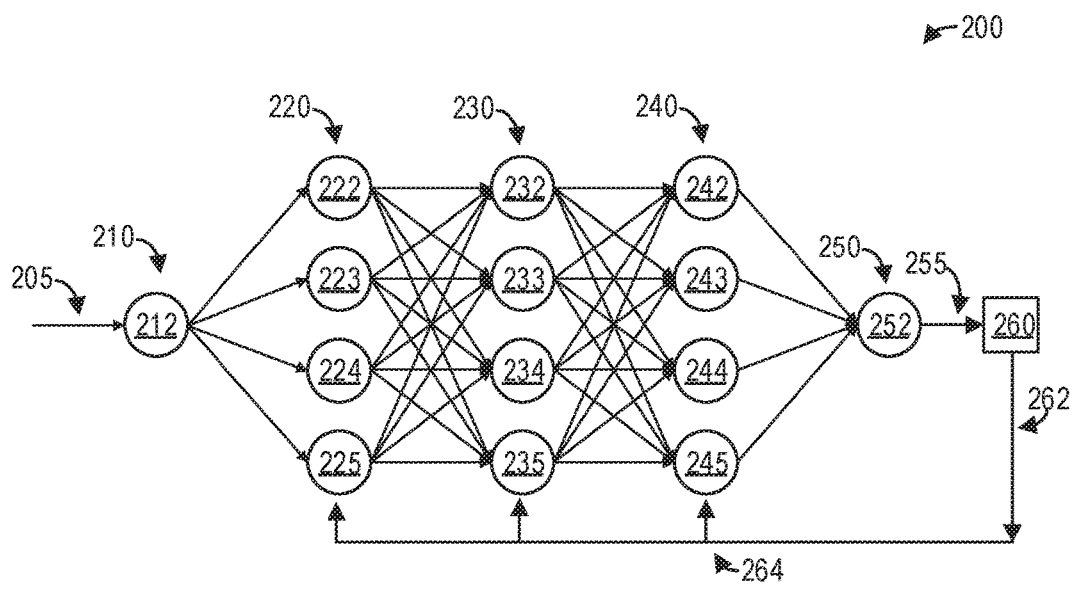
FIG. 2 shows a high-level diagram illustrating an example deep neural network according to an embodiment.

FIG. 1 shows a schematic block diagram illustrating an example system 100 for training a centralized learning model with data from a plurality of imaging systems in accordance with an embodiment. The components of system 100 are depicted at a high-level to emphasize components of the system 100 that are relevant to the present disclosure, though it should be understood that the system 100 may include additional systems and components not depicted in FIG. 1.

The system 100 includes a plurality of imaging systems 101, including at least a first imaging system 110, a second imaging system 120, and a third imaging system 130. Though only three imaging systems 110, 120, and 130 are depicted, it should be appreciated that the plurality of imaging systems 101 may include any number of imaging systems. Each imaging system of the plurality of imaging systems may be located in different hospitals or other institutions.

Furthermore, the plurality of imaging systems 101 may comprise a same imaging modality. For example, each imaging system of the plurality of imaging systems 101 may comprise a CT imaging system. An example CT imaging system is described further herein with regard to FIGS. 5 and 6. As another example, each imaging system of the plurality of imaging systems 101 may comprise a magnetic resonance imaging (MM) system. As yet another example, each imaging system of the plurality of imaging systems 101 may comprise a positron emission tomography (PET) imaging system. As another example, each imaging system of the plurality of imaging systems 101 may comprise an ultrasound imaging system. In some examples, the plurality of imaging systems may comprise a multi-modality imaging system. For example, each imaging system of the plurality of imaging systems 101 may comprise a PET/CT imaging system.

The first imaging system 110 comprises a scanner 111, a processor 113, a non-transitory memory 114, a user interface 117, and a display device 118. The scanner 111 comprises the components of the first imaging system 110 configured to scan or image a subject. For example, if the first imaging system 110 comprises a CT imaging system, the scanner 111 comprises at least an x-ray tube and a detector, and in some examples may further comprise a gantry, a digital acquisition system (DAS), and other components necessary for scanning or imaging a subject. Additional components of a CT imaging system that may comprise the scanner 111 are described further herein with regard to FIGS. 5 and 6. As another example, if the first imaging system 110 comprises an ultrasound imaging system, the scanner 111 comprises at least an ultrasound transducer. Similar to the first imaging system 110, the second imaging system 120 includes a scanner 121, a processor 123, a non-transitory memory 124, a user interface 127, and a display device 128. Further, the third imaging system 130 comprises a scanner 131, a processor 133, a non-transitory memory 134, a user interface 137, and a display device 138.

Each imaging system of the plurality of imaging systems 101 includes a neural network trained to perform a task, including but not limited to image classification. As depicted, the first imaging system 110 includes a first neural network 115 stored in the non-transitory memory 114, the second imaging system 120 includes a second neural network 125 stored in the non-transitory memory 124, and the third imaging system 130 includes a third neural network 135 stored in the non-transitory memory 134.

Initially, the first neural network 115, the second neural network 125, and the third neural network 135 may comprise a same neural network. Over time, as the different imaging systems 110, 120, and 130 are used to image subjects and the corresponding neural networks 115, 125, and 135 are used to process the images or imaging data, the knowledge of the neural networks 115, 125, and 135 diverges. That is, the first neural network 115 is trained over time using imaging data acquired by the imaging system 110, the second neural network 125 is trained over time using imaging data acquired by the imaging system 120, and the third neural network 135 is trained over time using imaging data acquired by the imaging system 130.

The system 100 further comprises a server 150 configured to collect data from the plurality of imaging systems 101 for training a central neural network model 155. To that end, the server 150 comprises a processor 153 and a non-transitory memory 154 with the central deep neural network 155 stored thereon. Further, as the server 150 may be located at a different geographical location than the plurality of imaging systems 101, each imaging system of the plurality of imaging systems 101 is communicatively coupled to the server 150 via a network 140 such as the Internet. The central neural network 155 initially comprises the same neural network model as the first neural network 115, the second neural network 125, and the third neural network 135.

As discussed further herein, the server 150 aggregates training data received via the network 140 from each of the plurality of imaging systems 101 and trains the central neural network 155. After training the central neural network 155, the central neural network 155 is deployed to the plurality of imaging systems 101 to replace or update the neural networks 115, 125, and 135.

FIG. 2 shows a high-level diagram illustrating an example deep neural network model 200 according to an embodiment. The deep neural network 200 may comprise the neural networks 115, 125, 135, and 155 described hereinabove with regard to FIG. 1. As such, the deep neural network 200 may be trained to perform a task related to diagnostic imaging, such as automatically classifying organs in an image, as an illustrative and non-limiting example.

As depicted, the deep neural network 200 includes an input layer 210, a first hidden layer 220, a second hidden layer 230, a third hidden layer 240, and an output layer 250. Input layer 210 comprises a plurality of input nodes 212. As discussed further herein, an input 205 comprising imaging data (e.g., projection data) and/or image data (e.g., an image) is input to the input layer 210. The first hidden layer 220 includes a plurality of nodes 222, 223, 224, and 225. As depicted, each input node 212 is connected to each of the nodes 222, 223, 224, and 225 of the first hidden layer 220. The second hidden layer 230 includes a plurality of nodes 232, 233, 234, and 235. Each node 222, 223, 224, and 225 of the first hidden layer 220 is connected to each node 232, 233, 234, and 235 of the second hidden layer 230. The third hidden layer 240 includes a plurality of nodes 242, 243, 244, and 245. Each node 232, 233, 234, and 235 of the second hidden layer 230 is connected to each node 242, 243, 244, and 245 of the third hidden layer 240. The output layer 250 includes a plurality of output nodes 252. Each node 242, 243, 244, and 245 of the third hidden layer 240 is connected to each node 252 of the output layer 250. The output layer 250 generates an output 255 which comprises the result of the processing by the deep neural network 200.

The hidden nodes of the hidden layers 220, 230, and 240 receive one or more inputs and sums them to produce an output. The sums of each node are weighted, and the sum is passed through a non-linear activation function. The resulting output is then passed on to each node in the following layer.

The deep neural network 200 may therefore comprise a feedforward neural network. In some examples, the deep neural network 200 may learn through backpropagation. To minimize total error, gradient descent may be used to adjust each weight in proportion to the derivative of the error with respect to that weight, provided the non-linear activation functions are differentiable. Also, global optimization methods may be used to train the weights of the deep neural network 200.

The output of the output layer 250 is compared to a ground truth 260 to determine a loss function or error function 262. As discussed above, backpropagation may thus be used to generate weight updates 264 that are applied to each of the nodes. As discussed further herein, the weight updates 264 generated by the neural network models 115, 125, and 135 may be output to the server 150 in order to train the central neural network model 155. In this way, the training of an individual neural network model may be used to train another independent neural network model.

It should be understood that the deep neural network 200 is illustrative and non-limiting, as FIG. 2 illustrates a relatively small number of nodes for simplicity. For example, although only one input node 212 is depicted, it should be appreciated that input layer 210 may include any suitable number of input nodes 212. Similarly, although only one output node 252 is depicted, it should be appreciated that output layer 250 may include any suitable number of output nodes 252. Furthermore, three hidden layers 220, 230, and 240 are depicted in the deep neural network 200, though it should be appreciated that the deep neural network 200 may include at least two hidden layers, and in some examples may include more than three hidden layers. Furthermore, each of the hidden layers 220, 230, and 240 are depicted as comprising four nodes each, though it should be appreciated that each of the hidden layers 220, 230, and 240 may include any suitable number of nodes, and in some examples each hidden layer may include hundreds or even thousands of nodes.

Figure 3:
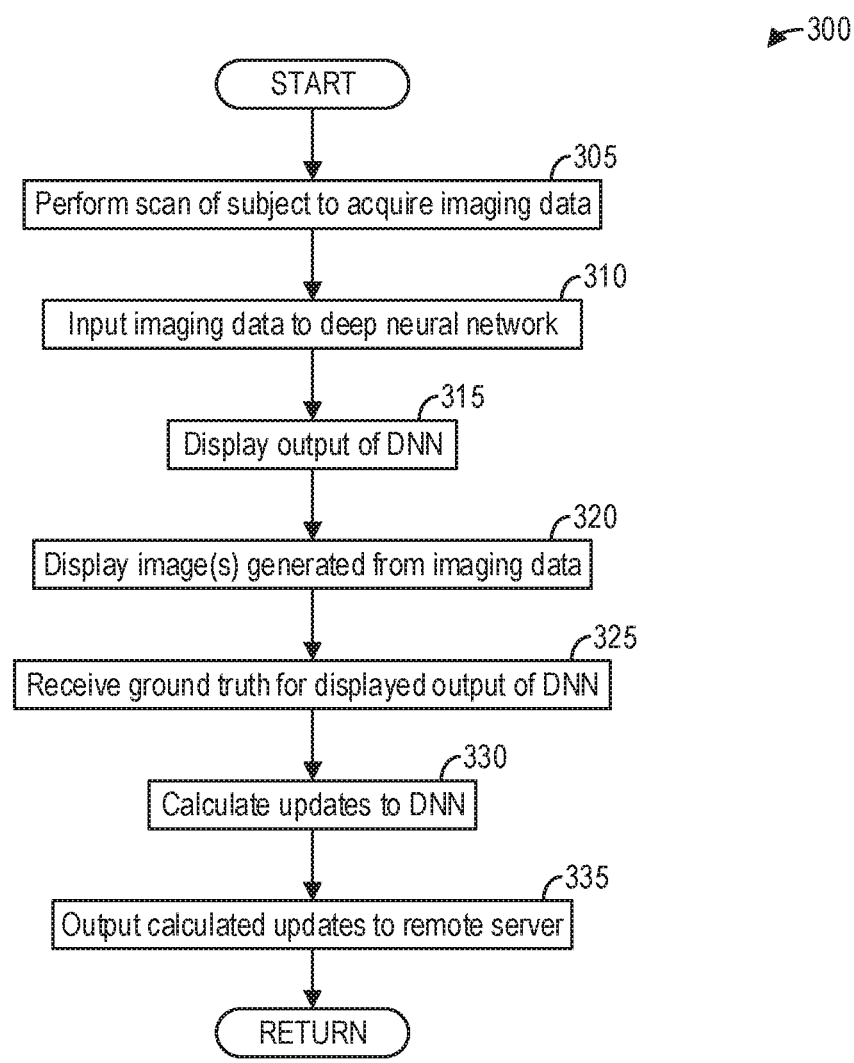
FIG. 3 shows a high-level flowchart illustrating an example method for generating deep learning training data with an imaging system according to an embodiment.

FIG. 3 shows a high-level flowchart illustrating an example method 300 for generating training information for a central learning model. In particular, method 300 relates to generating weight adjustments for a neural network and transmitting the weight adjustments to a central server for training. Method 300 is described with regard to the systems and components of FIGS. 1 and 2, though it should be appreciated that the method may be implemented with other systems and components without departing from the scope of the present disclosure. Method 300 may be implemented as executable instructions in non-transitory memory of an imaging system, such as imaging system 110, 120, and 130. For the purpose of clarity, method 300 is described herein from the perspective of imaging system 110.

Method 300 begins at 305. At 305, method 300 performs a scan of a subject to acquire imaging data. Performing a scan of the subject comprises controlling a scanner, such as scanner 111, to scan the subject to acquire the imaging data. Scanning a subject to acquire imaging data with a CT imaging system is described further herein with regard to FIGS. 5 and 6.

At 310, method 300 inputs the imaging data acquired at 305 to a deep neural network. For example, method 300 may input the imaging data into such as DNN 115. The DNN 115 processes the imaging data to generate an output.

At 315, method 300 displays the output of the DNN, for example via a display device such as display device 118. Further, at 320, method 300 displays one or more images reconstructed from the imaging data. Method 300 displays the one or more images reconstructed from the imaging data via a display device, such as display device 118. In some examples, method 300 displays the output of the DNN superimposed over the one or more images. In other examples, method 300 displays the output of the DNN adjacent to the one or more images via the display device 118.

At 325, method 300 receives a ground truth for the displayed output of the DNN. Method 300 receives the ground truth for the displayed output of the DNN via a user interface, such as user interface 117. The ground truth comprises the desired output of the DNN. For example, the ground truth comprises factual data regarding the output that is observed or measured by a human. In other words, the ground truth comprises the correct output that the DNN ideally should have output. As an illustrative and non-limiting example, if the task of the DNN is to classify organs in an image, the ground truth may comprise one or more labels of the organs in the image as identified by a human. In this example, an operator of the imaging system may view the image displayed at 320 and input, via the user interface 117, the ground truth comprising labels for one or more organs visible in the image. Method 300 thus receives the input via the user interface 117. The format of the ground truth thus corresponds to the format of the displayed output of the DNN. For example, if the task of the DNN is to segment organs in an image, the corresponding ground truth would comprise a segmentation of the organs in the image performed by an operator of the imaging system 110 via the user interface 117. In some examples, if the displayed output of the DNN is correct, the operator of the imaging system may simply confirm that the output of the DNN matches what the operator observes in the image.

At 330, method 300 calculates updates to the DNN based on the ground truth. In particular, method 300 uses backpropagation by gradient descent to calculate adjustments to the weights of the nodes in the DNN. In general for backpropagation, method 300 calculates a loss function that measures the difference between the output of the DNN and the ground truth, propagates the error backwards from the output nodes through the network, and then calculates the derivative of the loss function with respect to the weights of the DNN. In particular, method 300 uses gradient descent to calculate adjustments to the weights of the DNN that minimize the loss function. Backpropagation with gradient descent is well known in the art, and one of ordinary skill in the art will appreciate that regardless of the particular implementation of backpropagation, the method will calculate updates to the weights of the DNN. After applying the calculated updates to the DNN trains the DNN on the present case.

At 335, method 300 outputs the calculated updates to a remote server. For example, method 300 outputs the calculated updates to server 150 via a network 140. As discussed above, the calculated updates comprise the training of the DNN on the particular imaging case. By outputting the calculated updates to the server, the server may train a central DNN with the calculated updates. In this way, training performed locally (i.e., in the imaging system within a hospital) can be leveraged globally (i.e., for other imaging systems at other hospitals) without transmitting the patient image data itself. Method 300 then ends.

Figure 4:
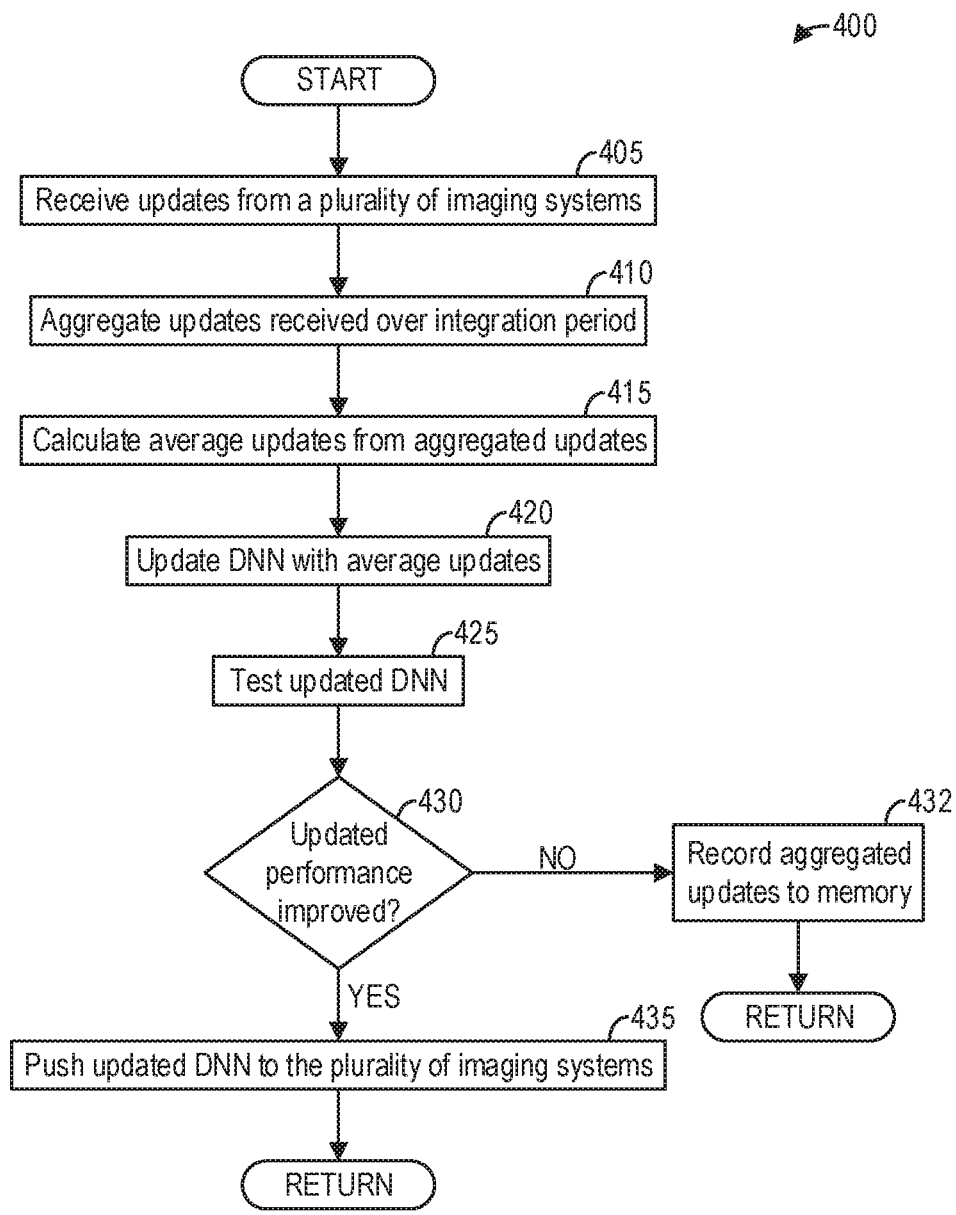
FIG. 4 shows a high-level flow chart illustrating an example method for centralized collection of deep learning training data according to an embodiment.

FIG. 4 shows a high-level flowchart illustrating an example method 400 for aggregating updates from a plurality of imaging systems. In particular, method 400 relates to training a central neural network model with network updates received from a plurality of imaging systems. Method 400 is described with regard to the systems and components of FIGS. 1 and 2, though it should be understood that the method may be implemented with other systems and components without departing from the scope of the present disclosure. Method 400 may be implemented as executable instructions in non-transitory memory 154 of server 150 and may be executed by the processor 153 of the server 150.

Method 400 begins at 405. At 405, method 400 receives updates from a plurality of imaging systems, such as the plurality of imaging systems 101. Method 400 may receive one or more updates from one or more imaging systems of the plurality of imaging systems 101. For example, method 400 receives updates generated by the first imaging system 110 for the first DNN 115, updates generated by the second imaging system 120 for the second DNN 125, and updates generated by the third imaging system 130 for the third DNN 135.

As discussed hereinabove with regard to FIG. 3, an update received from an imaging system, such as imaging system 110, comprises a set of weight adjustments calculated for the weights of a DNN for a single imaging case. As an illustrative and non-limiting example, an update may comprise an array or vector wherein each element of the array corresponds to a weight adjustment for a weight of the DNN. Thus, for a DNN with say, 1,000 nodes, an update may comprise a one-dimensional array with 1,000 elements, each element comprising a weight adjustment for a corresponding node.

It should be appreciated that method 400 may receive any number of updates from any of the plurality of imaging systems 101. As discussed further herein below, the number of updates received from any of the plurality of imaging systems 101 may depend on the length of an integration period for collecting updates, as well as the usage of a particular imaging system of the plurality of imaging systems 101. As an illustrative and non-limiting example, method 400 may receive one hundred updates from the first imaging system 110, zero updates from the second imaging system 120, and five updates from the third imaging system 130. In this example, the first imaging system 110 used the first DNN 115 one hundred times during the integration period, the second imaging system 120 used the second DNN 125 zero times during the integration period, and the third imaging system 130 used the third DNN 135 five times during the integration period.

At 410, method 400 aggregates the updates received from the plurality of imaging systems 101 over an integration period. For example, method 400 may concatenate the updates to form an array or matrix of updates. As an illustrative and non-limiting example, if an update comprises a vector with fifty elements (e.g., corresponding to a DNN with fifty nodes), and method 400 receives fifty updates from the plurality of imaging systems during an integration period, method 400 combines the fifty updates into a 50×50 matrix wherein each column corresponds to a different update and each row includes weight adjustments for a given node. The integration period comprises a predetermined duration of time during which method 400 aggregates updates received from the plurality of imaging systems before updating the central DNN. The integration period may be determined according to how often method 400 receives updates from the plurality of imaging systems. As an example, the integration period may comprise twenty-four hours. Method 400 would thus aggregate updates received from the plurality of imaging systems 101 during a twenty-four hour period.

It should be understood that the integration period may be less than twenty-four hours. For example, the integration period may comprise an hour if method 400 receives a substantial number of updates from the plurality of imaging systems 101. It should also be understood that the integration period may be greater than twenty-four hours. For example, the integration period may comprise a week, such that method 400 aggregates all updates received from the plurality of imaging systems 101 in a week.

In some examples, method 400 may aggregate updates according to a number of updates received in addition to or as an alternative to an integration period. For example, method 400 may wait to accumulate a threshold number of updates, rather than aggregating updates received within a certain duration. As another example, method 400 may aggregate updates once the number of updates received from the plurality of imaging systems 101 reaches a threshold number of updates, and otherwise may aggregate updates received during the integration period if the total number of updates received is less than the threshold number of updates.

After aggregating the updates received during the integration period at 410, method 400 continues to 415. At 415, method 400 calculates average updates from the aggregated updates. That is, method 400 calculates the average of the aggregated updates for each node of the DNN. For the illustrative example discussed hereinabove wherein fifty updates are received from the plurality of imaging systems 101 for a DNN with fifty nodes and aggregated into a 50×50 matrix, method 400 averages the elements in each row of the matrix to create a vector of fifty elements, wherein each element comprises an average update for a corresponding node.

Continuing at 420, method 400 updates a central DNN, such as central DNN 155, with the average updates. That is, the average update for each node calculated at 415 is applied to the corresponding node of the central DNN 155. As a result, the updated DNN 155 is equivalent to a DNN that has been trained directly with the imaging data generated by the plurality of imaging systems 101.

In some examples, method 400 may promptly deploy the updated DNN 155 to each imaging system of the plurality of imaging systems 101. The updated DNN 155 would replace the corresponding DNNs installed in the imaging systems 101. For example, the first imaging system 110 receives the updated DNN 155 from the server 150 and replaces the first DNN 115 with the updated DNN 155, the second imaging system 120 receives the updated DNN 155 from the server 150 and replaces the second DNN 125 with the updated DNN 155, and the third imaging system 130 receives the updated DNN 155 and replaces the third DNN 135 with the updated DNN 155. However, in other examples, as discussed further herein, method 400 may first test the updated DNN prior to deployment to ensure that the performance of the updated DNN is satisfactory.

Thus, continuing at 425, method 400 tests the updated DNN with a test dataset to evaluate the performance of the updated DNN. That is, method 400 inputs test cases in the test dataset to the updated DNN and calculates one or more performance measures of the updated DNN based on the error of each test case. The one or more performance measures may include, but are not limited to, a root mean squared error, a mean absolute error, and percent good classification.

At 430, method 400 determines if the performance of the updated DNN is improved with respect to the previous iteration of the DNN. The performance of the updated DNN is improved if the performance measure obtained at 425 is improved with respect to a measurement of the same performance measure for the previous iteration of the DNN. For example, if the mean absolute error of the updated DNN is less than the mean absolute error of the previous iteration of the DNN, then the performance of the updated DNN is improved.

If the performance of the updated DNN is not improved ("NO"), method 400 proceeds to 432. At 432, method 400 records the aggregated updates to memory. The aggregated updates may thus be retrievable from the memory for later review or aggregation with another set of updates. Method 400 then ends.

However, referring again to 430, if the performance of the updated DNN is improved ("YES"), method 400 proceeds to 435. At 435, method 400 pushes the updated DNN to each imaging system of the plurality of imaging systems 101. Method 400 then ends.

Figure 5:
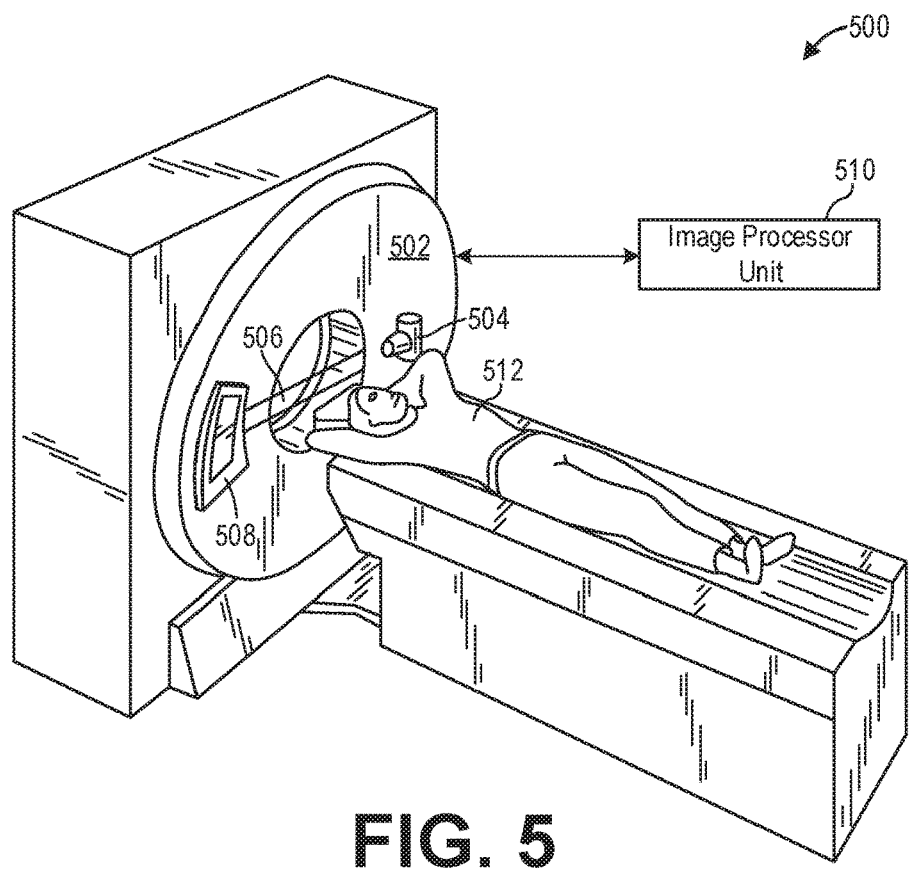
FIG. 5 shows a pictorial view of an imaging system according to an embodiment.

FIG. 5 illustrates an exemplary CT system 500 configured to allow fast and iterative image reconstruction. Particularly, the CT system 500 is configured to image a subject 512 such as a patient, an inanimate object, one or more manufactured parts, and/or foreign objects such as dental implants, stents, and/or contrast agents present within the body. In one embodiment, the CT system 500 includes a gantry 502, which in turn, may further include at least one x-ray radiation source 504 configured to project a beam of x-ray radiation 506 for use in imaging the subject 512. Specifically, the x-ray radiation source 504 is configured to project the x-rays 506 towards a detector array 508 positioned on the opposite side of the gantry 502. Although FIG. 5 depicts only a single x-ray radiation source 504, in certain embodiments, multiple x-ray radiation sources may be employed to project a plurality of x-rays 506 for acquiring projection data corresponding to the subject 512 at different energy levels.

In certain embodiments, the CT system 500 further includes an image processor unit 510 configured to reconstruct images of a target volume of the subject 512 using an iterative or analytic image reconstruction method. For example, the image processor unit 510 may use an analytic image reconstruction approach such as filtered backprojection (FBP) to reconstruct images of a target volume of the patient. As another example, the image processor unit 510 may use an iterative image reconstruction approach such as advanced statistical iterative reconstruction (ASIR), conjugate gradient (CG), maximum likelihood expectation maximization (MLEM), model-based iterative reconstruction (MBIR), and so on to reconstruct images of a target volume of the subject 512.

In some known CT imaging system configurations, a radiation source projects a fan-shaped beam which is collimated to lie within an X-Y plane of a Cartesian coordinate system and generally referred to as an "imaging plane." The radiation beam passes through an object being imaged, such as the patient or subject 512. The beam, after being attenuated by the object, impinges upon an array of radiation detectors. The intensity of the attenuated radiation beam received at the detector array is dependent upon the attenuation of a radiation beam by the object. Each detector element of the array produces a separate electrical signal that is a measurement of the beam attenuation at the detector location. The attenuation measurements from all the detectors are acquired separately to produce a transmission profile.

In some CT systems, the radiation source and the detector array are rotated with a gantry within the imaging plane and around the object to be imaged such that an angle at which the radiation beam intersects the object constantly changes. A group of radiation attenuation measurements, i.e., projection data, from the detector array at one gantry angle is referred to as a "view." A "scan" of the object includes a set of views made at different gantry angles, or view angles, during one revolution of the radiation source and detector. It is contemplated that the benefits of the methods described herein accrue to medical imaging modalities other than CT, so as used herein the term view is not limited to the use as described above with respect to projection data from one gantry angle. The term "view" is used to mean one data acquisition whenever there are multiple data acquisitions from different angles, whether from a CT, PET, or SPECT acquisition, and/or any other modality including modalities yet to be developed as well as combinations thereof in fused embodiments.

In an axial scan, the projection data is processed to reconstruct an image that corresponds to a two-dimensional slice taken through the object. One method for reconstructing an image from a set of projection data is referred to in the art as the filtered backprojection (FBP) technique. Transmission and emission tomography reconstruction techniques also include statistical iterative methods such as maximum likelihood expectation maximization (MLEM) and ordered-subsets expectation reconstruction techniques as well as iterative reconstruction techniques. This process converts the attenuation measurements from a scan into integers called "CT numbers" or "Hounsfield units," which are used to control the brightness of a corresponding pixel on a display device.

To reduce the total scan time, a "helical" scan may be performed. To perform a helical scan, the patient is moved while the data for the prescribed number of slices is acquired. Such a system generates a single helix from a cone beam helical scan. The helix mapped out by the cone beam yields projection data from which images in each prescribed slice may be reconstructed.

As used herein, the phrase "reconstructing an image" is not intended to exclude embodiments of the present disclosure in which data representing an image is generated but a viewable image is not. Therefore, as used herein the term "image" broadly refers to both viewable images and data representing a viewable image. However, many embodiments generate (or are configured to generate) at least one viewable image.

Figure 6:
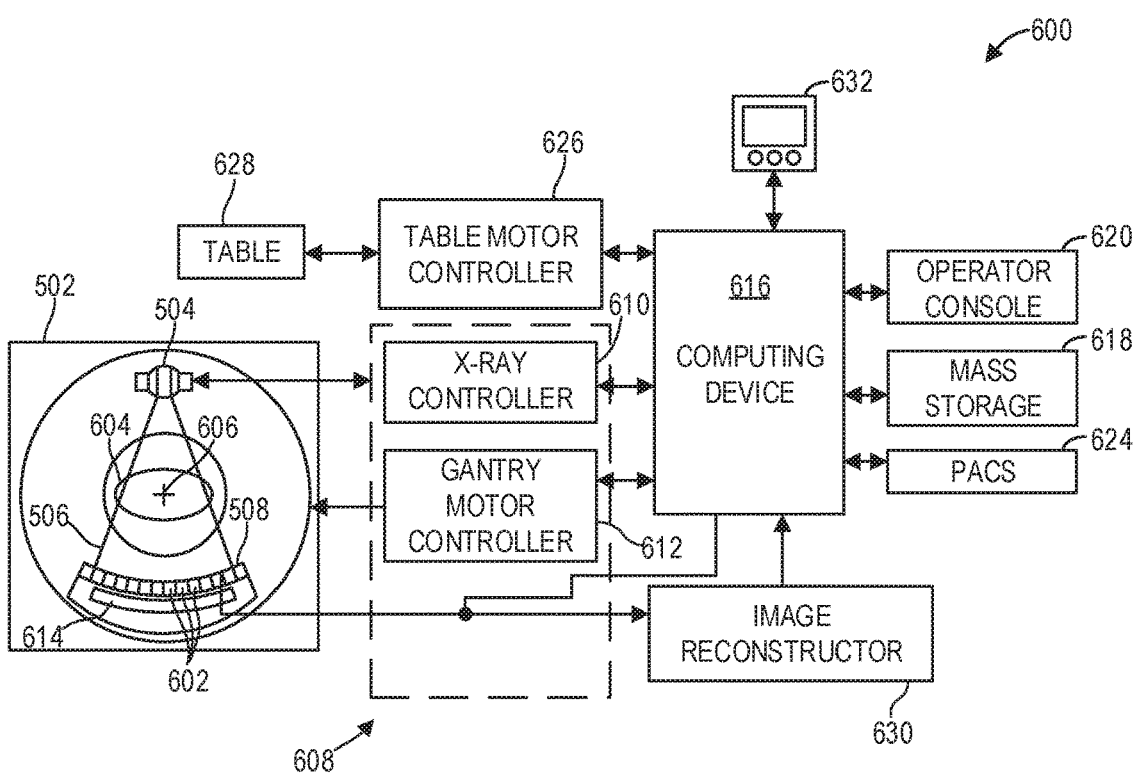
FIG. 6 shows a block schematic diagram of an exemplary imaging system according to an embodiment.

FIG. 6 illustrates an exemplary imaging system 600 similar to the CT system 500 of FIG. 5. In accordance with aspects of the present disclosure, the imaging system 600 is configured to output intermediate representations of imaging data from a deep learning algorithm to a central server. In one embodiment, the imaging system 600 includes the detector array 508 (see FIG. 5). The detector array 508 further includes a plurality of detector elements 602 that together sense the x-ray beams 506 (see FIG. 5) that pass through a subject 604 such as a patient to acquire corresponding projection data. Accordingly, in one embodiment, the detector array 508 is fabricated in a multi-slice configuration including the plurality of rows of cells or detector elements 602. In such a configuration, one or more additional rows of the detector elements 602 are arranged in a parallel configuration for acquiring the projection data.

In certain embodiments, the imaging system 600 is configured to traverse different angular positions around the subject 604 for acquiring desired projection data. Accordingly, the gantry 502 and the components mounted thereon may be configured to rotate about a center of rotation 606 for acquiring the projection data, for example, at different energy levels. Alternatively, in embodiments where a projection angle relative to the subject 604 varies as a function of time, the mounted components may be configured to move along a general curve rather than along a segment of a circle.

As the x-ray radiation source 504 and the detector array 508 rotate, the detector array 508 collects data of the attenuated x-ray beams. The data collected by the detector array 508 undergoes pre-processing and calibration to condition the data to represent the line integrals of the attenuation coefficients of the scanned subject 604. The processed data are commonly called projections.

In dual or multi-energy imaging, two or more sets of projection data are typically obtained for the imaged object at different tube peak kilovoltage (kVp) levels, which change the peak and spectrum of energy of the incident photons comprising the emitted x-ray beams or, alternatively, at a single tube kVp level or spectrum with an energy resolving detector of the detector array 508.

The acquired sets of projection data may be used for basis material decomposition (BMD). During BMD, the measured projections are converted to a set of density line-integral projections. The density line-integral projections may be reconstructed to form a density map or image of each respective basis material, such as bone, soft tissue, and/or contrast agent maps. The density maps or images may be, in turn, associated to form a volume rendering of the basis material, for example, bone, soft tissue, and/or contrast agent, in the imaged volume.

Once reconstructed, the basis material image produced by the imaging system 600 reveals internal features of the subject 604, expressed in the densities of the two basis materials. The density image may be displayed to show these features. In traditional approaches to diagnosis of medical conditions, such as disease states, and more generally of medical events, a radiologist or physician would consider a hard copy or display of the density image to discern characteristic features of interest. Such features might include lesions, sizes and shapes of particular anatomies or organs, and other features that would be discernable in the image based upon the skill and knowledge of the individual practitioner.

In one embodiment, the imaging system 600 includes a control mechanism 608 to control movement of the components such as rotation of the gantry 502 and the operation of the x-ray radiation source 504. In certain embodiments, the control mechanism 608 further includes an x-ray controller 610 configured to provide power and timing signals to the x-ray radiation source 504. Additionally, the control mechanism 608 includes a gantry motor controller 612 configured to control a rotational speed and/or position of the gantry 502 based on imaging requirements.

In certain embodiments, the control mechanism 608 further includes a data acquisition system (DAS) 614 configured to sample analog data received from the detector elements 602 and convert the analog data to digital signals for subsequent processing. The data sampled and digitized by the DAS 614 is transmitted to a computer or computing device 616. In one example, the computing device 616 stores the data in a storage device such as mass storage 618. The mass storage 618, for example, may include a hard disk drive, a floppy disk drive, a compact disk-read/write (CD-R/W) drive, a Digital Versatile Disc (DVD) drive, a flash drive, and/or a solid-state storage drive.

Additionally, the computing device 616 provides commands and parameters to one or more of the DAS 614, the x-ray controller 610, and the gantry motor controller 612 for controlling system operations such as data acquisition and/or processing. In certain embodiments, the computing device 616 controls system operations based on operator input. The computing device 616 receives the operator input, for example, including commands and/or scanning parameters via an operator console 620 operatively coupled to the computing device 616. The operator console 620 may include a keyboard (not shown) and/or a touchscreen to allow the operator to specify the commands and/or scanning parameters.

Although FIG. 6 illustrates only one operator console 620, more than one operator console may be coupled to the imaging system 600, for example, for inputting or outputting system parameters, requesting examinations, and/or viewing images. Further, in certain embodiments, the imaging system 600 may be coupled to multiple displays, printers, workstations, and/or similar devices located either locally or remotely, for example, within an institution or hospital, or in an entirely different location via one or more configurable wired and/or wireless networks such as the Internet and/or virtual private networks.

In one embodiment, for example, the imaging system 600 either includes or is coupled to a picture archiving and communications system (PACS) 624. In an exemplary implementation, the PACS 624 is further coupled to a remote system such as a radiology department information system, hospital information system, and/or to an internal or external network (not shown) to allow operators at different locations to supply commands and parameters and/or gain access to the image data.

The computing device 616 uses the operator-supplied and/or system-defined commands and parameters to operate a table motor controller 626, which in turn, may control a table 628 which may comprise a motorized table. Particularly, the table motor controller 626 moves the table 628 for appropriately positioning the subject 604 in the gantry 502 for acquiring projection data corresponding to the target volume of the subject 604.

As previously noted, the DAS 614 samples and digitizes the projection data acquired by the detector elements 602. Subsequently, an image reconstructor 630 uses the sampled and digitized x-ray data to perform high-speed reconstruction. Although FIG. 6 illustrates the image reconstructor 630 as a separate entity, in certain embodiments, the image reconstructor 630 may form part of the computing device 616. Alternatively, the image reconstructor 630 may be absent from the imaging system 600 and instead the computing device 616 may perform one or more of the functions of the image reconstructor 630. Moreover, the image reconstructor 630 may be located locally or remotely, and may be operatively connected to the imaging system 600 using a wired or wireless network. Particularly, one exemplary embodiment may use computing resources in a "cloud" network cluster for the image reconstructor 630.

In one embodiment, the image reconstructor 630 stores the images reconstructed in the storage device or mass storage 618. Alternatively, the image reconstructor 630 transmits the reconstructed images to the computing device 616 for generating useful patient information for diagnosis and evaluation. In certain embodiments, the computing device 616 transmits the reconstructed images and/or the patient information to a display 632 communicatively coupled to the computing device 616 and/or the image reconstructor 630.

The various methods and processes described further herein may be stored as executable instructions in non-transitory memory on a computing device in imaging system 600. For example, image reconstructor 630 may include such executable instructions in non-transitory memory, and may apply the methods described herein to reconstruct an image from scanning data. In another embodiment, computing device 616 may include the instructions in non-transitory memory, and may apply the methods described herein, at least in part, to a reconstructed image after receiving the reconstructed image from image reconstructor 630. In yet another embodiment, the methods and processes described herein may be distributed across image reconstructor 630 and computing system 616.

In one embodiment, the display 632 allows the operator to evaluate the imaged anatomy. The display 632 may also allow the operator to select a volume of interest (VOI) and/or request patient information, for example, via a graphical user interface (GUI) for a subsequent scan or processing.

A technical effect of the disclosure is the transmission of neural network updates to a server for training a central neural network. Another technical effect of the disclosure is the averaging of updates applied to a plurality of neural networks to train a central neural network. Yet another technical effect of the disclosure is the deployment of an updated neural network to a plurality of imaging systems. Another technical effect of the disclosure is the acquisition of imaging data for training a neural network. Another technical effect of the disclosure is the display of a reconstructed image with a neural network output superimposed over the image.

In one embodiment, a method for an imaging system comprises performing a scan of a subject to acquire imaging data, training a deep neural network on the imaging data to obtain updates to the deep neural network, and transmitting the updates to a server for training a central deep neural network.

In a first example of the method, training the deep neural network on the imaging data to obtain updates to the deep neural network comprises: inputting the imaging data to the deep neural network; displaying an output of the deep neural network and an image reconstructed from the imaging data; receiving a ground truth for the deep neural network; and calculating the updates to the deep neural network according to an error between the output and the ground truth. In a second example of the method optionally including the first example, calculating the updates to the deep neural network according to the error between the output and the ground truth comprises performing backpropagation on the deep neural network according to the error. In a third example of the method optionally including one or more of the first and second examples, displaying the output and the image comprises displaying, via a display device of the imaging system, the output superimposed on the image. In a fourth example of the method optionally including one or more of the first through third examples, displaying the output and the image comprises displaying, via a display device of the imaging system, the output adjacent to the image. In a fifth example of the method optionally including one or more of the first through fourth examples, the deep neural network and the central deep neural network share a same neural network architecture. In a sixth example of the method optionally including one or more of the first through fifth examples, the method further comprises aggregating the updates with other updates generated for the deep neural network. In a seventh example of the method optionally including one or more of the first through sixth examples, the method further comprises calculating average updates from the aggregated updates. In an eighth example of the method optionally including one or more of the first through seventh examples, transmitting the updates to the server comprises transmitting the average updates to the server. In a ninth example of the method optionally including one or more of the first through eighth examples, training the deep neural network on the imaging data comprises inputting one of the imaging data or an image reconstructed from the image data to the deep neural network.

In another embodiment, a system comprises: an imaging system comprising a scanner for scanning a subject to acquire imaging data, a processor, and a non-transitory memory storing a deep neural network; and a server comprising a processor and a non-transitory memory storing a central deep neural network, the server communicatively coupled to the imaging system via a network, wherein the imaging system is configured with executable instructions in the non-transitory memory of the imaging system that when executed cause the processor of the imaging system to calculate updates to the deep neural network when training the deep neural network on the imaging data, and transmit the updates to the server for training the central deep neural network.

In a first example of the system, the server is configured with executable instructions in the non-transitory memory of the server that when executed cause the processor of the server to receive the updates, aggregate the updates with other updates received from a plurality of imaging systems during an integration period, calculate average updates from the updates and the other updates received during the integration period, and apply the average updates to the central deep neural network to obtain an updated deep neural network. In a second example of the system optionally including the first example, the server is further configured with executable instructions in the non-transitory memory of the server that when executed cause the processor of the server to transmit the updated deep neural network to the imaging system to replace the deep neural network. In a third example of the system optionally including one or more of the first and second examples, the server is further configured with executable instructions in the non-transitory memory of the server that when executed cause the processor of the server to test the updated deep neural network with a test dataset to determine if a performance measure of the updated deep neural network is improved with respect to a previous iteration of the central deep neural network.

In yet another embodiment, an imaging system comprises an x-ray source that emits a beam of x-rays towards a subject to be imaged, a detector that receives the x-rays attenuated by the subject, a data acquisition system (DAS) operably connected to the detector, and a computing device operably connected to the DAS and configured with executable instructions in non-transitory memory that when executed cause the computing device to: control the x-ray source to perform a scan of the subject; receive, via the DAS, projection data obtained during the scan; train a deep neural network on the projection data to obtain updates to the deep neural network; and transmit the updates to a server for training a central deep neural network.

In a first example of the imaging system, training the deep neural network on the projection data to obtain the updates to the deep neural network comprises inputting the projection data to the deep neural network to obtain an output of the deep neural network, receiving a ground truth for the deep neural network, and calculating the updates to the deep neural network according to an error between the output and the ground truth. In a second example of the imaging system optionally including the first example, the imaging system further comprises an operator console configured to receive input and communicatively coupled to the computing device, wherein the computing device is further configured with instructions in non-transitory memory that when executed cause the computing device to receive the ground truth via the operator console. In a third example of the imaging system optionally including one or more of the first and second examples, the imaging system further comprises a display device, wherein the computing device is further configured with instructions in non-transitory memory that when executed cause the computing device to display, via the display device, the output of the deep neural network and an image reconstructed from the projection data. In a fourth example of the imaging system optionally including one or more of the first through third examples, the computing device is further configured with instructions in non-transitory memory that when executed cause the computing device to receive, from the server, an updated deep neural network that is trained with the updates in addition to updates generated by other imaging systems. In a fifth example of the imaging system optionally including one or more of the first through fourth examples, the computing device is further configured with instructions in non-transitory memory that when executed cause the computing device to process projection data with the updated deep neural network.

As used herein, an element or step recited in the singular and proceeded with the word "a" or "an" should be understood as not excluding plural of said elements or steps, unless such exclusion is explicitly stated. Furthermore, references to "one embodiment" of the present invention are not intended to be interpreted as excluding the existence of additional embodiments that also incorporate the recited features. Moreover, unless explicitly stated to the contrary, embodiments "comprising," "including," or "having" an element or a plurality of elements having a particular property may include additional such elements not having that property. The terms "including" and "in which" are used as the plain-language equivalents of the respective terms "comprising" and "wherein." Moreover, the terms "first," "second," and "third," etc. are used merely as labels, and are not intended to impose numerical requirements or a particular positional order on their objects.

This written description uses examples to disclose the invention, including the best mode, and also to enable a person of ordinary skill in the relevant art to practice the invention, including making and using any devices or systems and performing any incorporated methods. The patentable scope of the invention is defined by the claims, and may include other examples that occur to those of ordinary skill in the art. Such other examples are intended to be within the scope of the claims if they have structural elements that do not differ from the literal language of the claims, or if they include equivalent structural elements with insubstantial differences from the literal languages of the claims.

The invention claimed is:

1. A method for an imaging system, comprising:
   performing a scan of a subject to acquire imaging data;
   training a deep neural network on the imaging data and a ground truth to obtain updates to the deep neural network, the ground truth received from a user of the imaging system;
   transmitting the updates to a server for training a central deep neural network; and
   receiving, from the server, an update to the deep neural network based on the updates if the updates improve a performance measure of the central deep neural network.

2. The method of claim 1, wherein training the deep neural network on the imaging data to obtain the updates to the deep neural network comprises:
   inputting the imaging data to the deep neural network;
   displaying an output of the deep neural network and an image reconstructed from the imaging data;
   receiving, from the user via a user interface, the ground truth for the deep neural network; and
   calculating the updates to the deep neural network according to an error between the output and the ground truth.

3. The method of claim 2, wherein calculating the updates to the deep neural network according to the error between the output and the ground truth comprises performing backpropagation on the deep neural network according to the error.

4. The method of claim 2, wherein displaying the output and the image comprises displaying, via a display device of the imaging system, the output superimposed on the image.

5. The method of claim 2, wherein displaying the output and the image comprises displaying, via a display device of the imaging system, the output adjacent to the image.

6. The method of claim 1, wherein the deep neural network and the central deep neural network share a same neural network architecture.

7. The method of claim 1, further comprising aggregating the updates with other updates generated for the deep neural network.

8. The method of claim 7, further comprising calculating average updates from the aggregated updates.

9. The method of claim 8, wherein transmitting the updates to the server comprises transmitting the average updates to the server.

10. The method of claim 1, wherein training the deep neural network on the imaging data comprises inputting one of the imaging data or an image reconstructed from the imaging data to the deep neural network.

11. A system, comprising:
    an imaging system comprising a scanner for scanning a subject to acquire imaging data, a processor, and a non-transitory memory storing a deep neural network; and
    a server comprising a processor and a non-transitory memory storing a central deep neural network, the server communicatively coupled to the imaging system via a network;
    wherein the imaging system is configured with executable instructions in the non-transitory memory of the imaging system that when executed cause the processor of the imaging system to calculate updates to the deep neural network when training the deep neural network on the imaging data, and transmit the updates to the server for training the central deep neural network; and
    wherein the server is configured with executable instructions in the non-transitory memory of the server that when executed cause the processor of the server to update the central deep neural network based on the updates, test the updated central deep neural network with a test dataset to determine a performance measure of the updated central deep neural network, and transmit updates of the updated central deep neural network to a plurality of imaging systems including the imaging system responsive to the performance measure indicating improvement of the updated central deep neural network.

12. The system of claim 11, wherein the server is configured with executable instructions in the non-transitory memory of the server that when executed cause the processor of the server to receive the updates, aggregate the updates with other updates received from the plurality of imaging systems during an integration period, calculate average updates from the updates and the other updates received during the integration period, and apply the average updates to the central deep neural network to obtain an updated deep neural network.

13. The system of claim 12, wherein the server is further configured with executable instructions in the non-transitory memory of the server that when executed cause the processor of the server to transmit the updated deep neural network to the imaging system to replace the deep neural network.

14. The system of claim 13, wherein the server is further configured with executable instructions in the non-transitory memory of the server that when executed cause the processor of the server to test the updated deep neural network with the test dataset to determine if the performance measure of the updated deep neural network is improved with respect to a previous iteration of the central deep neural network.

15. An imaging system, comprising:
an x-ray source that emits a beam of x-rays towards a subject to be imaged;
a detector that receives the x-rays attenuated by the subject;
a data acquisition system (DAS) operably connected to the detector; and
a computing device operably connected to the DAS and configured with executable instructions in non-transitory memory that when executed cause the computing device to:
control the x-ray source to perform a scan of the subject;
receive, via the DAS, projection data obtained during the scan;
train a deep neural network on the projection data to obtain updates to the deep neural network;
transmit the updates to a server for training a central deep neural network; and
receive, from the server, an update to the deep neural network based on the updates if the updates improve a performance measure of the central deep neural network.

16. The imaging system of claim 15, wherein training the deep neural network on the projection data to obtain the updates to the deep neural network comprises inputting the projection data to the deep neural network to obtain an output of the deep neural network, receiving a ground truth for the deep neural network, and calculating the updates to the deep neural network according to an error between the output and the ground truth.

17. The imaging system of claim 16, further comprising an operator console configured to receive input and communicatively coupled to the computing device, wherein the computing device is further configured with instructions in non-transitory memory that when executed cause the computing device to receive the ground truth via the operator console.

18. The imaging system of claim 16, further comprising a display device, wherein the computing device is further configured with instructions in non-transitory memory that when executed cause the computing device to display, via the display device, the output of the deep neural network and an image reconstructed from the projection data.

19. The imaging system of claim 16, wherein the computing device is further configured with instructions in non-transitory memory that when executed cause the computing device to receive, from the server, an updated deep neural network that is trained with the updates in addition to updates generated by other imaging systems.

20. The imaging system of claim 19, wherein the computing device is further configured with instructions in non-transitory memory that when executed cause the computing device to process projection data with the updated deep neural network.

* * * * *